United States Patent
RaginiDAS et al.

(10) Patent No.: US 8,279,513 B2
(45) Date of Patent: Oct. 2, 2012

(54) ELECTROCHROMIC MATERIALS AND ELECTROCHROMIC DEVICES USING THE SAME

(75) Inventors: Rupasree RaginiDAS, Suwon-si (KR); Chang Ho Noh, Suwon-si (KR); Ji Min Lee, Goyang-si (KR)

(73) Assignee: Samsung Electronics Co., Ltd. (KR)

( * ) Notice: Subject to any disclaimer, the term of this patent is extended or adjusted under 35 U.S.C. 154(b) by 18 days.

(21) Appl. No.: 13/083,059

(22) Filed: Apr. 8, 2011

(65) Prior Publication Data

US 2011/0184181 A1 Jul. 28, 2011

Related U.S. Application Data

(62) Division of application No. 12/360,679, filed on Jan. 27, 2009, now Pat. No. 7,944,597.

(30) Foreign Application Priority Data

Sep. 2, 2008 (KR) .................. 10-2008-0086451

(51) Int. Cl.
*G02F 1/153* (2006.01)
*G02B 5/23* (2006.01)

(52) U.S. Cl. ........................................ 359/273; 252/586
(58) Field of Classification Search .................. 359/265, 359/273; 252/586

See application file for complete search history.

(56) References Cited

U.S. PATENT DOCUMENTS

| | | | |
|---|---|---|---|
| 6,241,916 B1 * | 6/2001 | Claussen et al. | ............. 252/583 |
| 7,619,803 B2 | 11/2009 | Kokeguchi et al. | |
| 2005/0179012 A1 | 8/2005 | Kwon et al. | |
| 2006/0110638 A1 | 5/2006 | Corr et al. | |

FOREIGN PATENT DOCUMENTS

| | | |
|---|---|---|
| WO | 2004/067673 | 8/2004 |
| WO | 2006/129424 | 12/2006 |

* cited by examiner

*Primary Examiner* — William Choi
(74) *Attorney, Agent, or Firm* — Cantor Colburn LLP

(57) ABSTRACT

Disclosed herein are novel electrochromic materials. The electrochromic materials are viologens into which an imidazole derivative is asymmetrically introduced. The electrochromic materials can be used in a variety of electrochromic displays, including electrochromic windows and smart windows. Also disclosed herein are electrochromic devices that use the electrochromic materials.

3 Claims, 3 Drawing Sheets

ELECTROCHROMIC MATERIALS AND ELECTROCHROMIC DEVICES USING THE SAME

CROSS-REFERENCE TO RELATED APPLICATION

This application is a divisional of U.S. application Ser. No. 12/360,679, filed on Jan. 27, 2009, which claims priority to Korean Patent Application No. 10-2008-0086451, filed on Sep. 2, 2008, and all the benefits accruing therefrom under 35 U.S.C. §119, the contents of which in its entirety are herein incorporated by reference.

BACKGROUND

1. Field

This disclosure is directed to novel electrochromic materials and electrochromic devices that use the electrochromic materials. More specifically, the electrochromic materials are viologens into which an imidazole derivative is introduced asymmetrically (hereinafter "benzimidazole-derivatized asymmetric viologens").

2. Description of the Related Art

Electrochromism is the phenomenon displayed by some materials that reversibly change color when a voltage is applied to them. In other words, an electrochromic material is one that changes color upon applying an electrical field to it. The material undergoes reversible changes in optical properties by an electrochemical redox reaction.

Electrochromic devices that take advantage of the electrochromic phenomenon have various advantages over other materials used in similar applications such as high reflectivity without a need for an external light source, excellent flexibility and portability. Electrochromic materials are also lighter in weight, and are therefore expected to be useful as flat-panel displays (hereinafter "FPDs"). In particular, electrochromic devices are receiving a great deal of attention because they can be used as E-paper, an electronic medium potentially capable of replacing paper.

Examples of the electrochromic materials may include inorganic compounds such as tungsten oxides, molybdenum oxides, and the like, and organic compounds such as pyridine, aminoquinone, azine compounds, and the like. While blue and green electrochromic materials are known (i.e., they are known to exist in the form of nano-electrochromic forms), red electrochromic materials are not yet discovered.

Organic electrochromic materials are disadvantageous when compared with inorganic electrochromic materials in terms of long-term stability, but have advantages in that they can be used in flexible substrates and can also be used to form thin films by wet processing. Based on these advantages, a great deal of research has been conducted on organic electrochromic materials.

SUMMARY

Disclosed herein is an electrochromic material represented by the following Formula 1 or 2:

Formula (1)

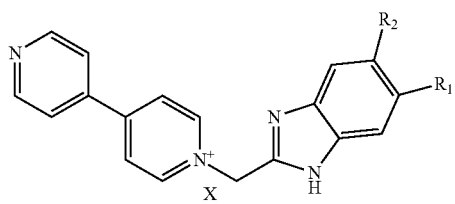

wherein $R_1$ and $R_2$ are each independently selected from the group consisting of hydrogen, halogen, CN, OH, COOH, $C_1$-$C_{20}$ alkyl, $C_3$-$C_{20}$ cycloalkyl, $C_2$-$C_{20}$ alkenyl, $C_1$-$C_{20}$ alkoxy and $C_5$-$C_{12}$ aryl, and wherein X is selected from the group consisting of halides, $PF_6^-$, $BF_4^-$, $BH_4^-$ and $CF_3SO_3^-$; or Formula (2)

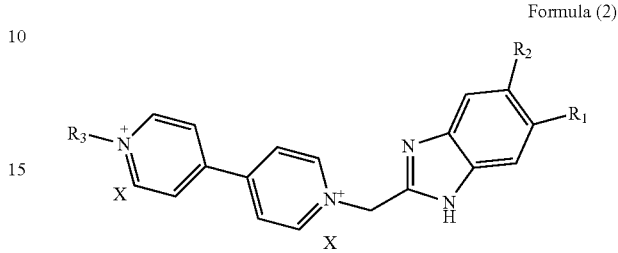

wherein $R_1$ and $R_2$ are each independently selected from the group consisting of hydrogen, halogen, CN, OH, COOH, $C_1$-$C_{20}$ alkyl, $C_3$-$C_{20}$ cycloalkyl, $C_2$-$C_{20}$ alkenyl, $C_1$-$C_{20}$ alkoxy and $C_5$-$C_{12}$ aryl, wherein each X is selected from the group consisting of halides, $PF_6^-$, $BF_4^-$, $BH_4^-$ and $CF_3SO_3^-$, and wherein $R_3$ is selected from the group consisting of hydrogen, $C_1$-$C_{20}$ alkyl, $C_3$-$C_{20}$ cycloalkyl, $C_2$-$C_{20}$ alkenyl, $C_1$-$C_{20}$ alkoxy, $C_5$-$C_{12}$ aryl, $C_5$-$C_{12}$ heteroaryl, carbazolyl, fluorenyl and spirofluorenyl.

Specifically, the electrochromic material is a viologen into which an imidazole derivative is introduced asymmetrically (hereinafter "benzimidazole-derivatized asymmetric viologen").

Disclosed herein too is an exemplary embodiment of an electrochromic device where the electrochromic device includes a first transparent electrode, a second electrode that is opposedly disposed to the transparent electrode and an electrochromic layer interposed between the transparent electrode and the second electrode, and wherein the electrochromic layer contains the electrochromic material of Formula 1 or 2.

Disclosed herein too is an exemplary embodiment of an electrochromic including a first transparent electrode including a transparent substrate with a conductive layer formed thereon; an electrochromic layer disposed on the transparent electrode; an electrolyte layer; and a second electrode; the electrolyte layer and the second electrode being disposed on a side of the electrochromic layer that is opposed to a side that is in contact with the first transparent electrode; wherein the electrochromic layer contains an electrochromic material represented by the Formula 1 or 2.

BRIEF DESCRIPTION OF THE DRAWINGS

The above and other aspects, features and advantages of the present invention will become more readily apparent by describing in further detail exemplary embodiments thereof with reference to the accompanying drawings, in which.

DETAILED DESCRIPTION

Figure 1:
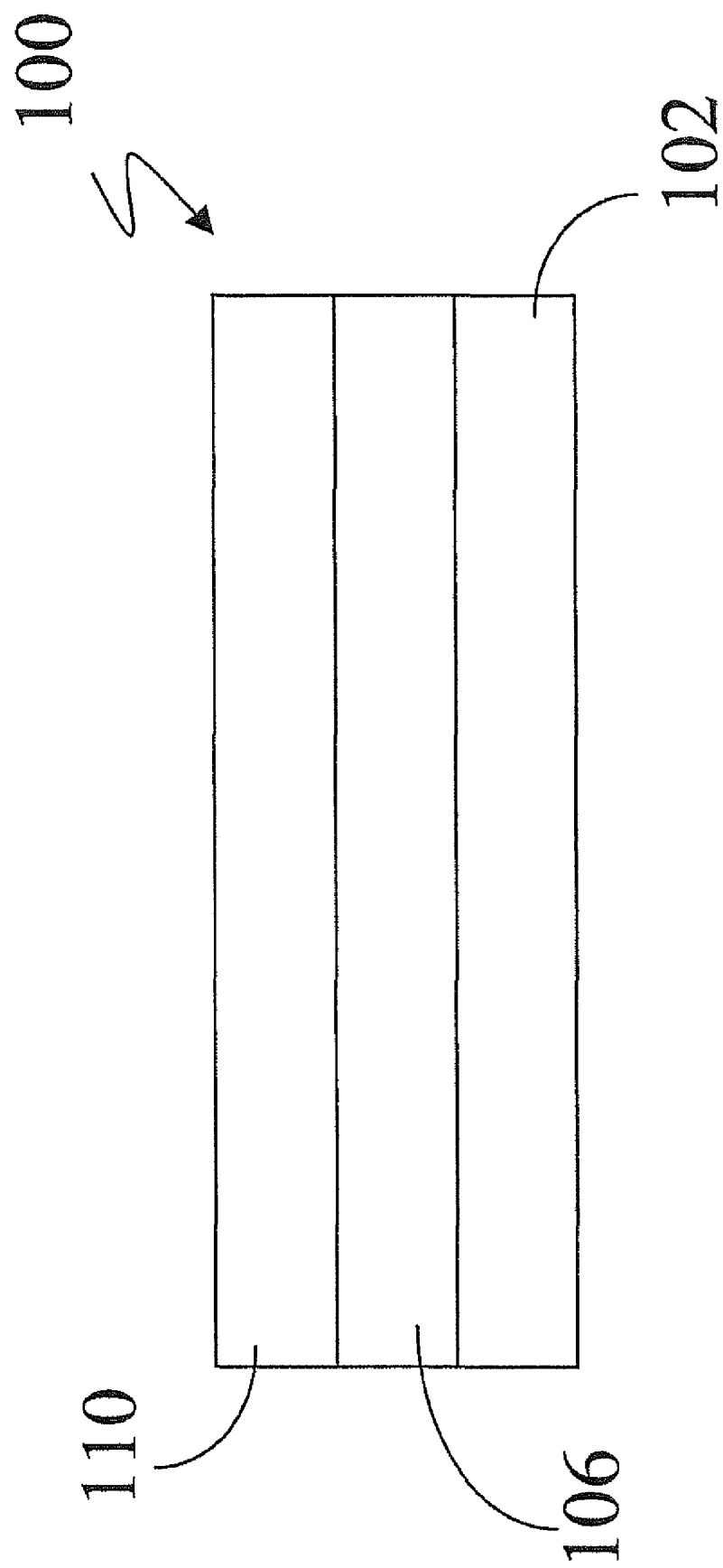
FIG. 1 is an exemplary embodiment depicting an electrochromic device that includes a first transparent electrode, an electrochromic layer and a second electrode.

The exemplary embodiments now will be described more fully hereinafter with reference to the accompanying drawings, in which embodiments are shown. These exemplary embodiments may, however, be embodied in many different forms and should not be construed as limited to the embodiments set forth herein. Rather, these exemplary embodiments are provided so that this disclosure will be thorough and complete, and will fully convey the scope of the exemplary embodiments to those skilled in the art. Like reference numerals refer to like elements throughout.

It will be understood that when an element is referred to as being "on" another element, it can be directly on, the other element or intervening elements may be present. As used herein, the term "and/or" includes any and all combinations of one or more of the associated listed items.

It will be understood that, although the terms first, second, third, or the like, may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the embodiments.

The terminology used herein is for the purpose of describing particular embodiments only and is not intended to be limiting of any particular embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, regions, integers, steps, operations, elements, components and/or groups, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompass both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the exemplary embodiments belong. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments of the exemplary embodiments. As such, variations from the shapes of the illustrations as a result, for example, of manufacturing techniques and/or tolerances, are to be expected. Thus, exemplary embodiments should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of example embodiments.

Hereinafter, the exemplary embodiments will be described in detail with reference to the accompanying drawings.

In one exemplary embodiment, the electrochromic material is represented by Formula 1 or 2:

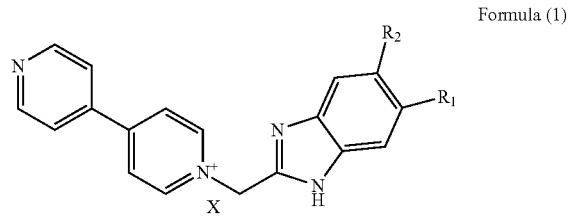

Formula (1)

wherein $R_1$ and $R_2$ are each independently selected from the group consisting of hydrogen, halogen, CN, OH, COOH, $C_1$-$C_{20}$ alkyl, $C_3$-$C_{20}$ cycloalkyl, $C_2$-$C_{20}$ alkenyl, $C_1$-$C_{20}$ alkoxy and $C_5$-$C_{12}$ aryl, and wherein X is selected from the group consisting of halides, $PF_6^-$, $BF_4^-$, $BH_4^-$ and $CF_3SO_3^-$; or

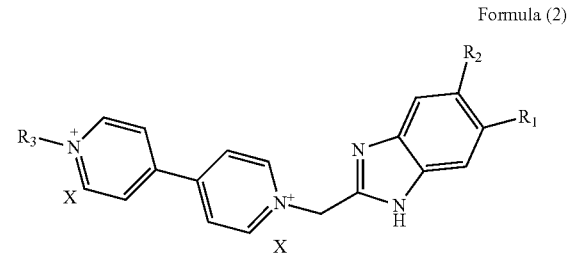

Formula (2)

wherein $R_1$ and $R_2$ are each independently selected from the group consisting of hydrogen, halogen, CN, OH, COOH, $C_1$-$C_{20}$ alkyl, $C_3$-$C_{20}$ cycloalkyl, $C_2$-$C_{20}$ alkenyl, $C_1$-$C_{20}$ alkoxy and $C_5$-$C_{12}$ aryl, wherein each X is selected from the group consisting of halides, $PF_6^-$, $BF_4^-$, $BH_4^-$ and $CF_3SO_3^-$, and wherein $R_3$ is selected from the group consisting of hydrogen, $C_1$-$C_{20}$ alkyl, $C_3$-$C_{20}$ cycloalkyl, $C_2$-$C_{20}$ alkenyl, $C_1$-$C_{20}$ alkoxy, $C_5$-$C_{12}$ aryl, $C_5$-$C_{12}$ heteroaryl, carbazolyl, fluorenyl and spirofluorenyl.

In one exemplary embodiment, $R_3$ in Formula 2 may have an end group selected from the group consisting of $CH_3$, OH, SH, COOH, $PO_3H_2$, halogen, CN and $COH_3$.

In one exemplary embodiment, X in Formula 1 or 2 represents a counter ion and can be a halide, $PF_6^-$, $BF_4^-$, $BH_4^-$ and $CF_3SO_3^-$.

In another exemplary embodiment, the electrochromic material can be represented by Formula 3:

Formula (3)

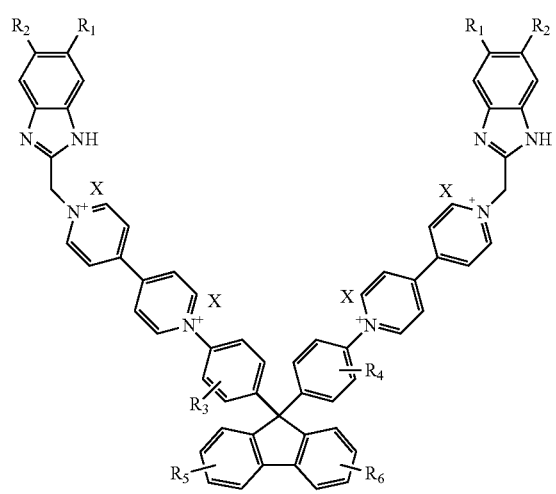

wherein $R_1$ and $R_2$ are each independently selected from the group consisting of hydrogen, halogen, CN, OH, COOH, $C_1$-$C_{20}$ alkyl, $C_3$-$C_{20}$ cycloalkyl, $C_2$-$C_{20}$ alkenyl, $C_1$-$C_{20}$ alkoxy and $C_5$-$C_{12}$ aryl, wherein each X is selected from the group consisting of halides, $PF_6^-$, $BF_4^-$, $BH_4^-$ and $CF_3SO_3^-$, and wherein $R_3$, $R_4$, $R_5$ and $R_6$ are independently selected from the group consisting of hydrogen, halogen, CN, OH, COOH, $C_1$-$C_{20}$ alkyl, $C_3$-$C_{20}$ cycloalkyl, $C_2$-$C_{20}$ alkenyl, $C_1$-$C_{20}$ alkoxy, $C_5$-$C_{12}$ aryl, $C_5$-$C_{12}$ heteroaryl, carbazolyl, fluorenyl and spirofluorenyl.

In one exemplary embodiment, at least one of $R_3$, $R_4$, $R_5$ and $R_6$ may additionally have an end group selected from the group consisting of $CH_3$, OH, SH, COOH, $PO_3H_2$, halogen, CN and $COH_3$.

Suitable examples of the electrochromic materials of Formula 1 or 2 can be represented by the compounds of Formulae 4 to 7:

Formula (4)

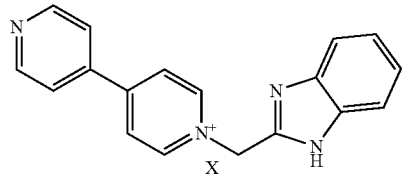

wherein X is selected from the group consisting of halides, $PF_6^-$, $BF_4^-$, $BH_4^-$ and $CF_3SO_3^-$;

Formula (5)

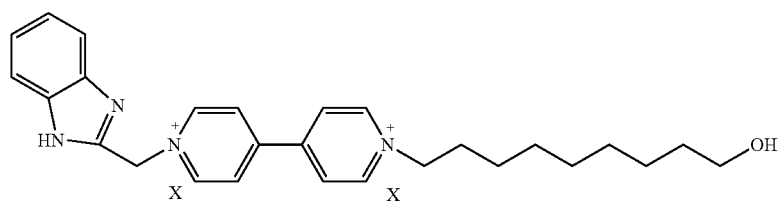

wherein each X is as defined in Formula 4;

Formula (6)

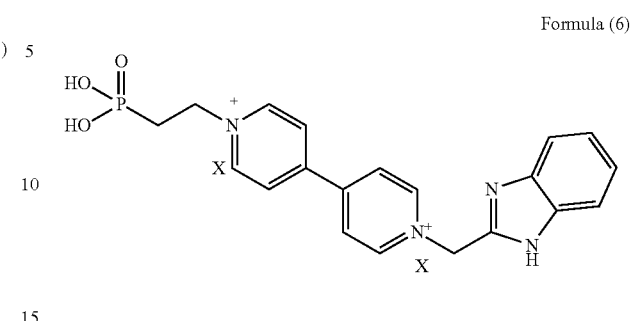

wherein each X is as defined in Formula 4;

Formula (7)

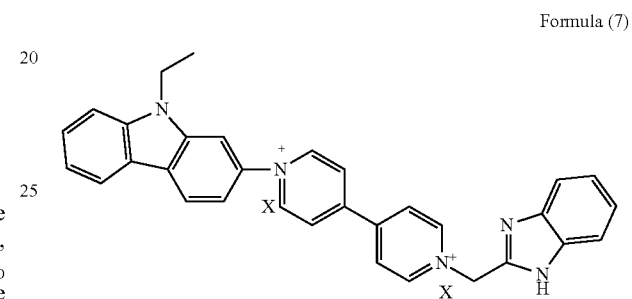

wherein each X is as defined in Formula 4.

Other examples of the electrochromic material of Formula 1 or 2 include:

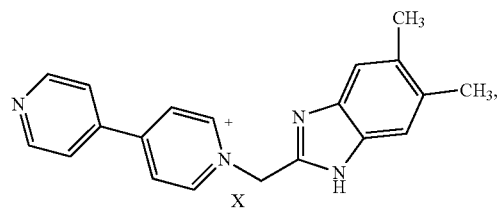

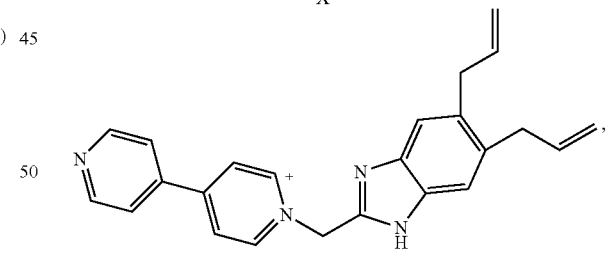

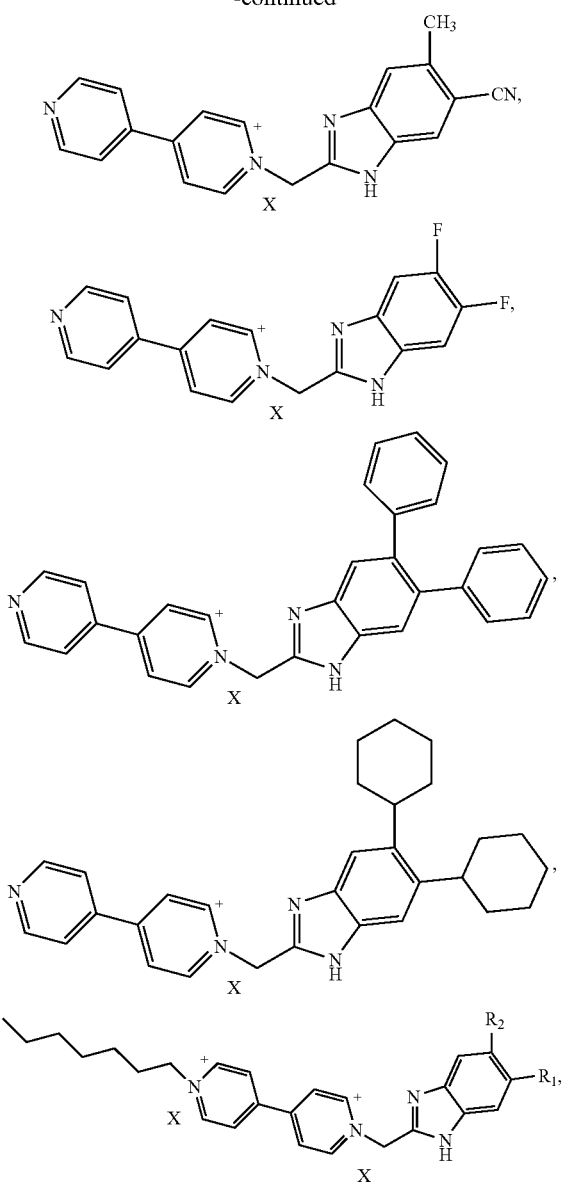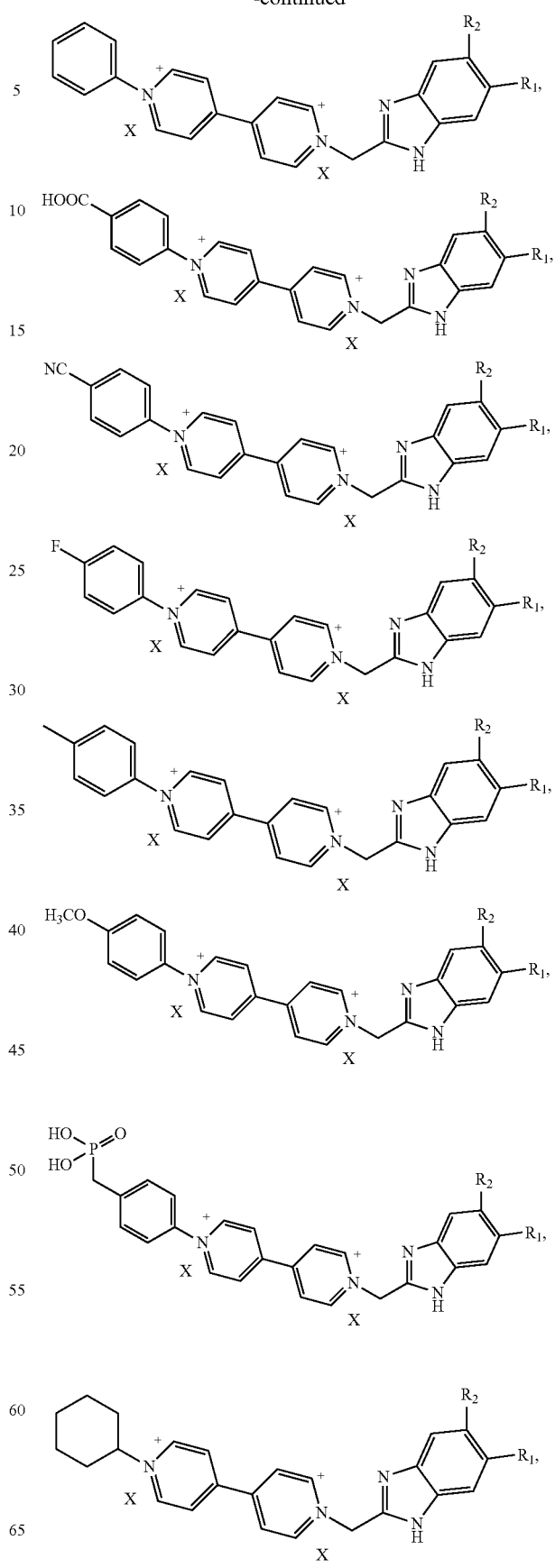

-continued

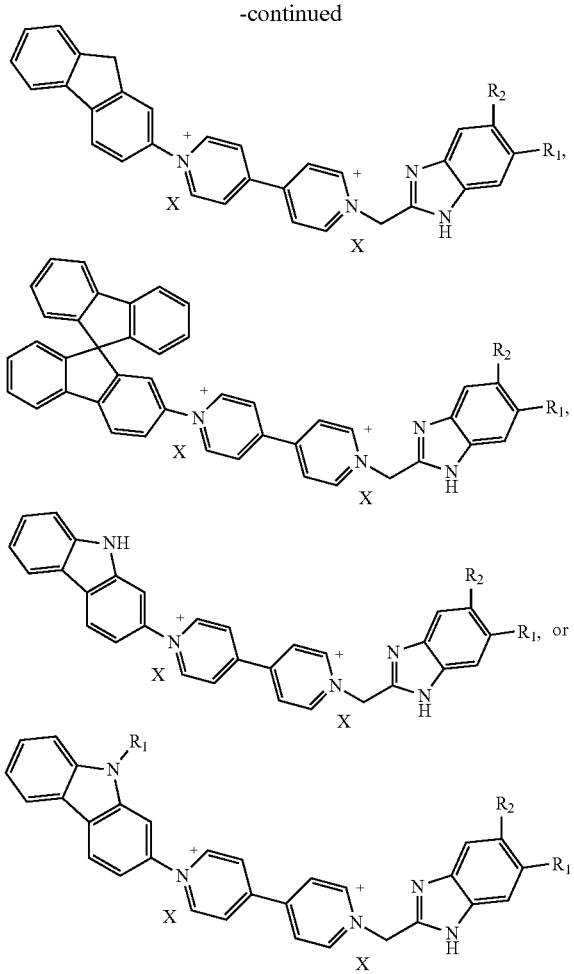

wherein $R_1$ and $R_2$ are each independently selected from the group consisting of hydrogen, halogen, CN, OH, COOH, $C_1$-$C_{20}$ alkyl, $C_3$-$C_{20}$ cycloalkyl, $C_2$-$C_{20}$ alkenyl, $C_1$-$C_{20}$ alkoxy and $C_5$-$C_{12}$ aryl, and wherein each X is selected from the group consisting of halides, $PF_6^-$, $BF_4^-$, $BH_4^-$ and $CF_3SO_3^-$.

In one exemplary embodiment, the electrochromic material of Formula 3 may be represented by a material having the structure shown in Formula 8:

Formula (8)

wherein each X is selected from the group consisting of halides, $PF_6^-$, $BF_4^-$, $BH_4^-$ and $CF_3SO_3^-$.

Suitable examples of the electrochromic material of Formula 3 include:

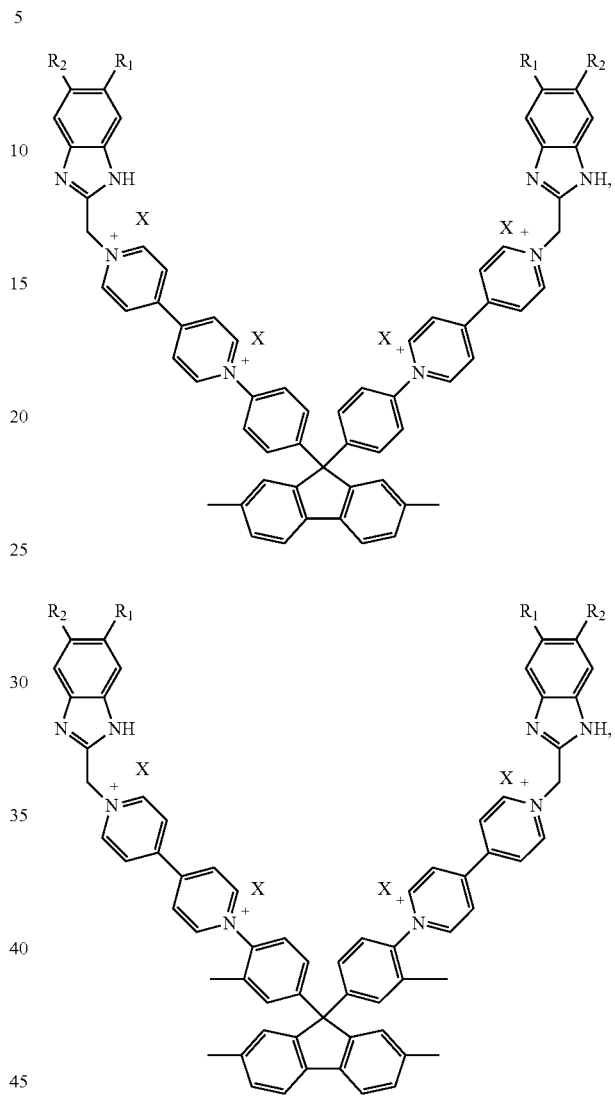

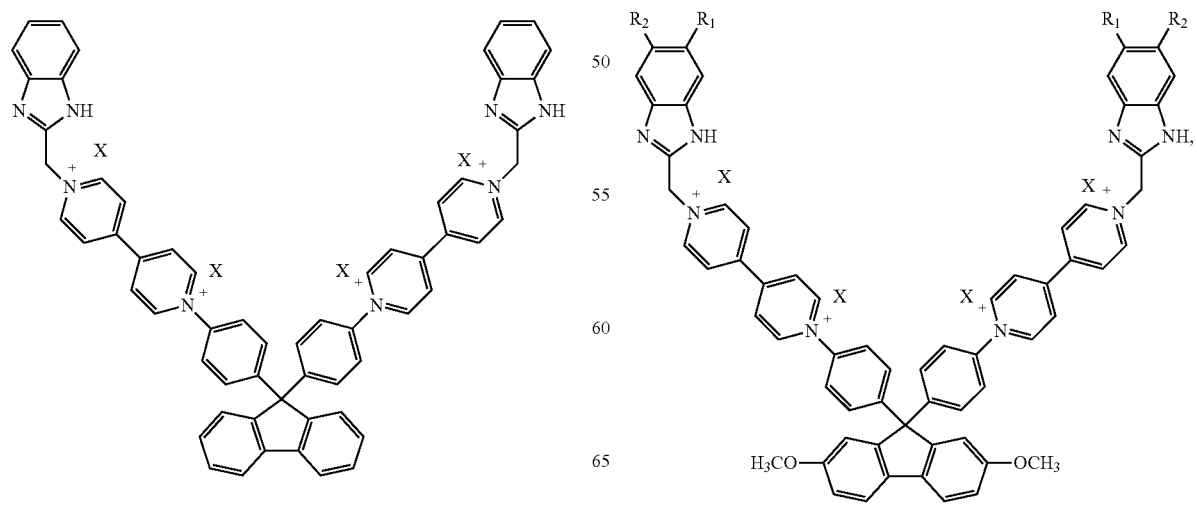

-continued

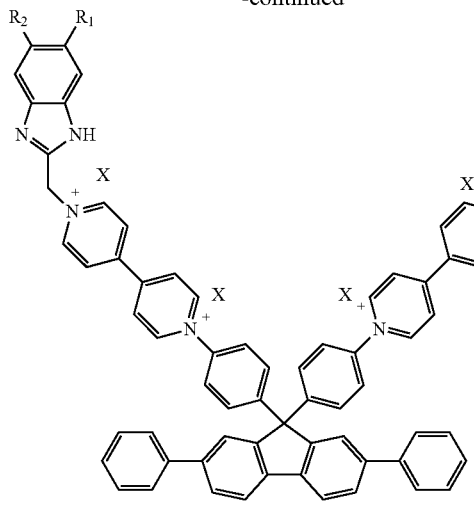

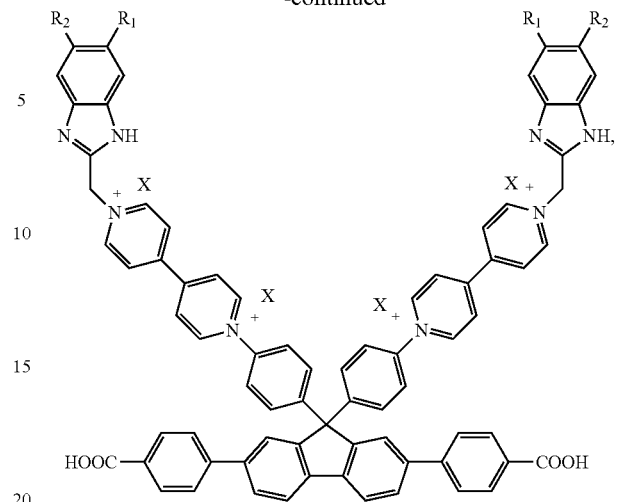

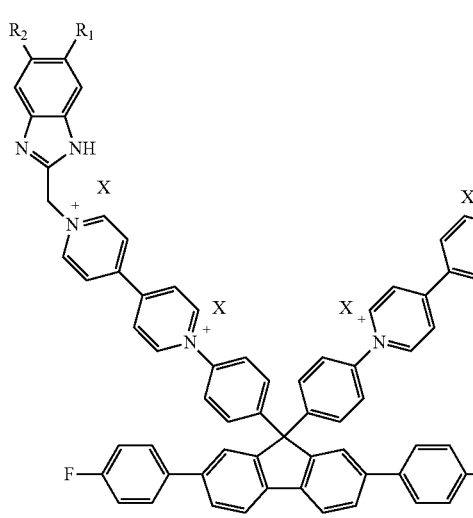

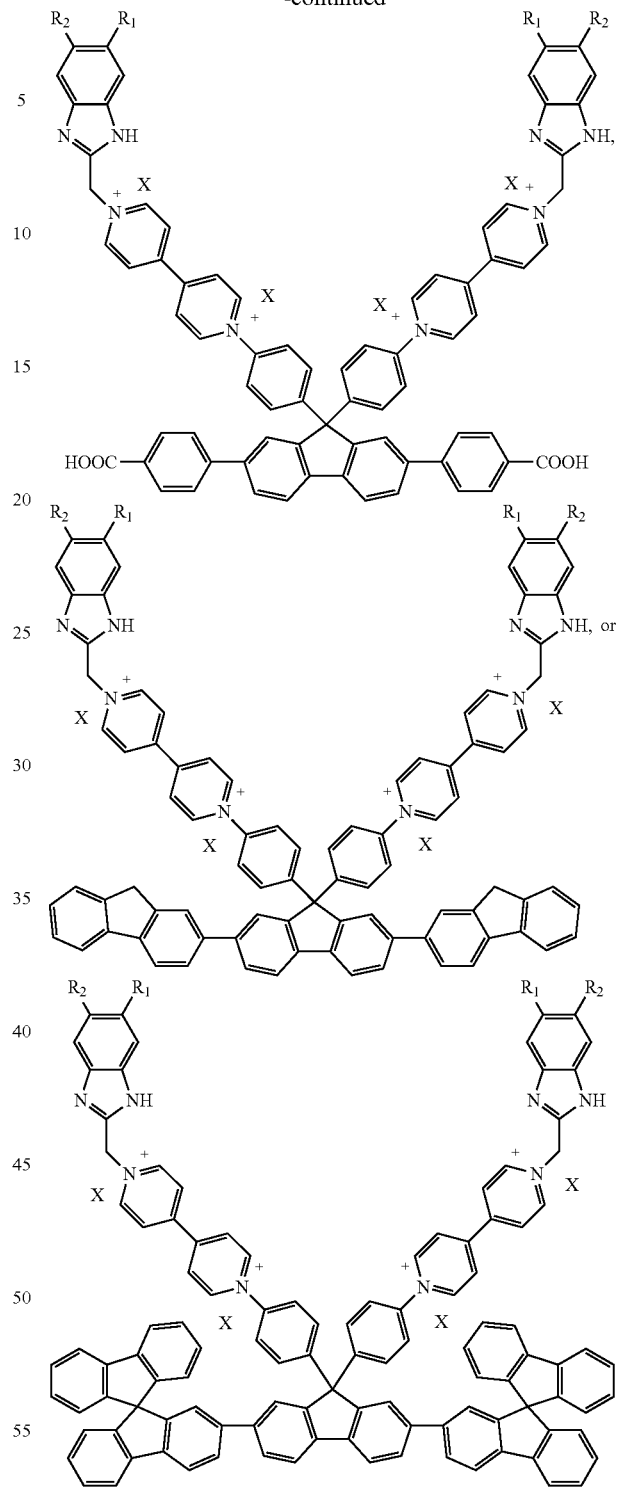

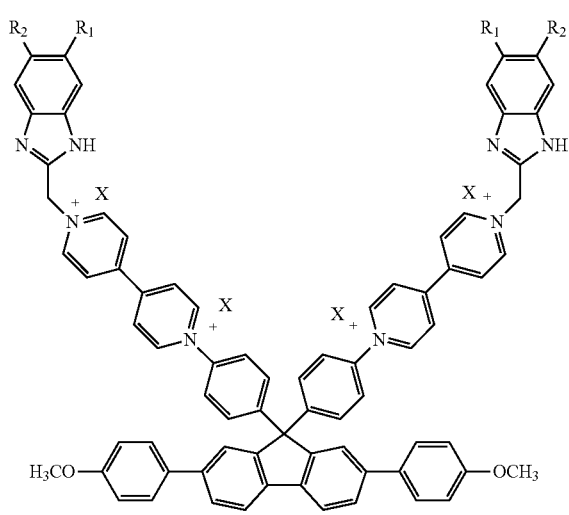

wherein $R_1$ and $R_2$ are each independently selected from the group consisting of hydrogen, halogen, CN, OH, COOH, $C_1$-$C_{20}$ alkyl, $C_3$-$C_{20}$ cycloalkyl, $C_2$-$C_{20}$ alkenyl, $C_1$-$C_{20}$ alkoxy and $C_5$-$C_{12}$ aryl, and wherein each X is selected from the group consisting of halides, $PF_6^-$, $BF_4^-$, $BH_4^-$ and $CF_3SO_3^-$.

The electrochromic materials can be used in a variety of electrochromic displays, including electrochromic windows and smart windows. In addition, the electrochromic materials are suitable for use in the fabrication of red-blue-green ("RGB") full-color electrochromic devices.

With reference now to the FIG. 1, in one exemplary embodiment, the electrochromic device 100 includes a first transparent electrode 102 and a second electrode 110 that is opposedly disposed to the first transparent electrode 102. An electrochromic layer 106 is interposed between the first transparent electrode 102 and the second electrode 110. The first transparent electrode 102 and the second electrode 110 are therefore disposed upon opposing surfaces of the electrochromic layer 106. The electrochromic layer 106 contains the electrochromic material of Formula 1, 2 or 3. In one embodiment, the first transparent electrode 102 and the second electrode 110 are in operative communication with opposing surfaces of the electrochromic layer 106.

Figure 2:
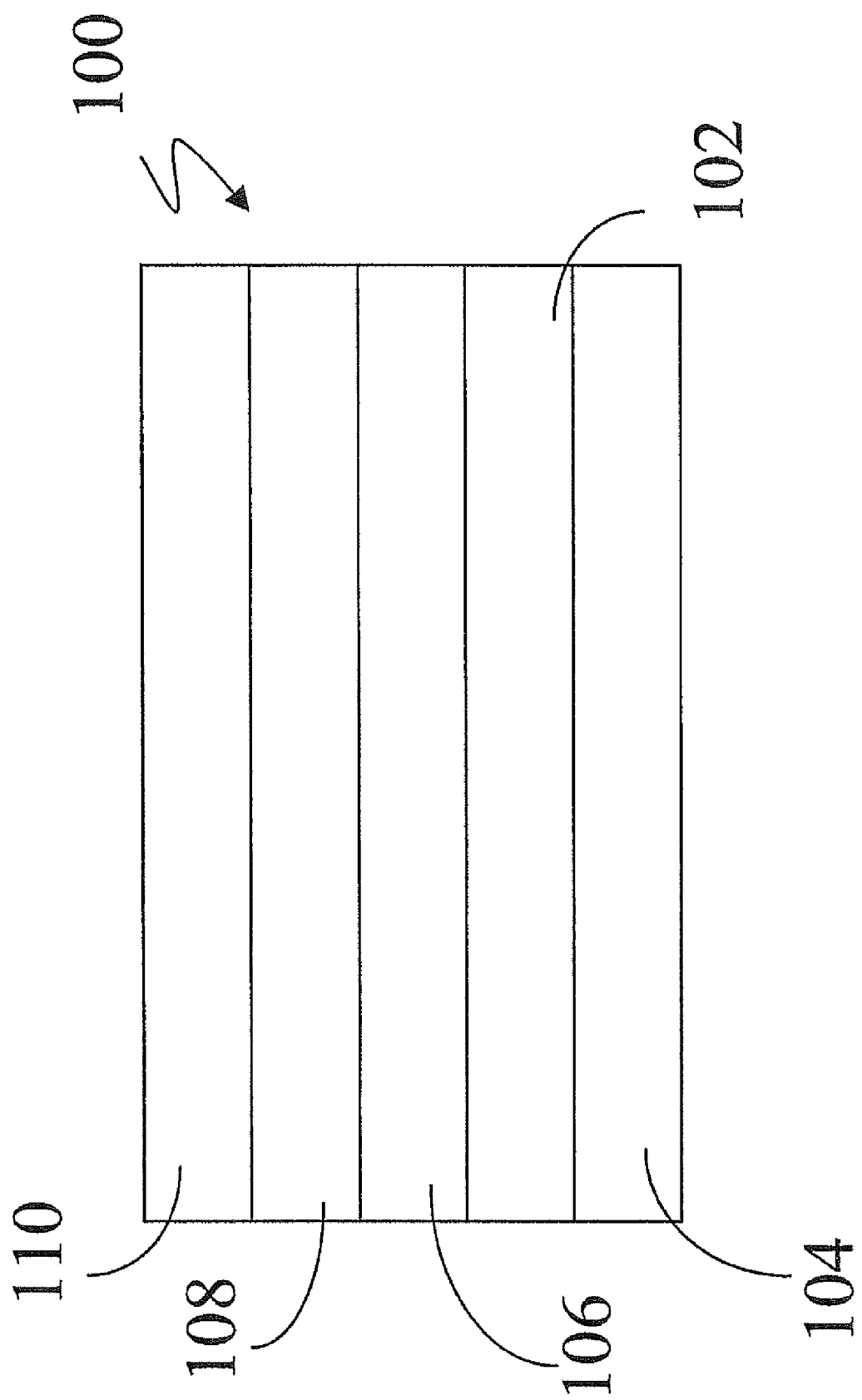
FIG. 2 is an exemplary embodiment depicting an electrochromic device that includes a first transparent electrode, a conductive layer, an electrochromic layer, an electrolyte layer and a second electrode.

With reference now to the FIG. 2, in another exemplary embodiment, the electrochromic device 100 includes a first transparent electrode 102 comprising a transparent substrate with a conductive layer 104 formed thereon. As can be seen in the FIG. 2, an electrochromic layer 106 is formed on the transparent electrode 102. The electrochromic layer 106 contains the electrochromic material of Formulas 1, 2 or 3. An electrolyte layer 108 and a second electrode 110 are disposed on a side of the electrochromic layer 106 that is opposed to the side that is in contact with the first transparent electrode 102. The electrolyte layer 108 is disposed between the electrochromic layer 106 and the second electrode 110.

In one exemplary embodiment, the electrochromic layer may be formed by adsorbing the electrochromic material on to nanostructured materials (e.g., materials that have nanopores). Exemplary nanostructured materials are titanium dioxide ($TiO_2$), zinc oxide (ZnO), tungsten oxide ($WO_3$) or a combination comprising at least one of the foregoing nanostructured materials.

In one embodiment, the nanostructures may have various shapes, including spheres, tetrahedrons, cylinders, rods, triangles, discs, tripods, tetrapods, cubes, boxes, stars, tubes, or a combination comprising at least one of the foregoing shapes.

The transparent substrate can include materials such as ceramics, polymers, or a combination comprising at least one of the foregoing materials. Examples of a transparent ceramic substrate include transparent inorganic substrates, exemplary embodiments of which include glass and quartz substrates. Examples of transparent plastics that can be used in the substrate are polyethylene terephthalate (PET), polyethylene naphthalate (PEN), polyethersulfone (PES), polycarbonate, polystyrene, polyalkylacrylates, polyacrylates, polypropylene or a combination comprising at least one of the foregoing plastics. Exemplary embodiments also include configurations having flexible substrates.

A transparent electrically conductive material can be coated on the transparent substrate to form the electrically conductive films. Examples of transparent electrically conductive materials are indium tin oxide (ITO), fluorine-doped tin oxide (FTO), transparent electrode materials that comprise carbon nanotubes (CNTs), transparent electrode materials that comprise electrically conductive polymers, such as, for example, polyacetylene, polypyrrole, polyaniline, polythiophene, or a combination comprising at least one of the foregoing electrically conductive materials.

Examples of electrochromic material are metal oxides, pyridine compounds, aminoquinone compounds viologens, and a combination comprising at least one of the foregoing electrochromic materials. Examples of suitable metal oxides for use in the electrochromic material are tungsten oxide, molybdenum oxide, or a combination comprising at least one of the foregoing electrochromic materials.

In one embodiment, the electrochromic layer may be formed using a solution of the electrochromic material in an electrolyte. The electrolyte provides ions and electrons (upon being subjected to an applied voltage), which interact with the electrochromic material and cause the electrochromic material to change color. Examples of suitable electrolytes are solutions of lithium salts, potassium salts and sodium salts in suitable solvents.

Any electrically conductive material may be used regardless of its transparency to form a conductive layer that constitutes the second electrode. Furthermore, in one exemplary embodiment, a counter material layer may be formed on the conductive material that constitutes the second electrode. The counter material layer can facilitate efficient electrochemical reactions of the electrochromic material.

In one embodiment, the electrochromic device may further include a white reflective layer that is disposed on the second electrode. Examples of materials that can be used to form the white reflective layer are titanium dioxide ($TiO_2$), barium sulfate ($BaSO_4$), aluminum oxide ($Al_2O_3$), zinc oxide (ZnO), magnesium oxide (MgO), or a combination comprising at least one of the foregoing materials. Particles whose size distribution is in the range of about 50 nanometers (nm) to about 500 nm are used to form the white reflective layer.

The conductive films of the first transparent electrode and the second electrode may function as an anode and a cathode respectively. A voltage applied between the first transparent electrode and the second electrode allows the electrochromic material to react with ions and electrons present in the electrolyte, resulting in a change in the color of the electrochromic material.

In one embodiment, the electrochromic device may turn red in response to an applied voltage when the device contains the electrochromic material of Formula 4. The electrochromic device may turn blue in response to an applied voltage when the device contains the electrochromic material of Formula 5. The electrochromic device may turn violet in response to an applied voltage when the device contains the electrochromic material of Formula 6. The electrochromic device may turn green in response to an applied voltage when the device contains the electrochromic material of Formula 7 or 8.

A more detailed description of exemplary embodiments will be described in more detail with reference to the following examples. However, these examples are given merely for the purpose of illustration and are not to be construed as limiting the scope of the embodiments.

PREPARATION OF ELECTROCHROMIC MATERIALS

EXAMPLE 1

Synthesis of Compound 1

The compound of Formula 1 ('Compound 1') was synthesized according to the following reaction scheme (1).

Reaction Scheme (1)

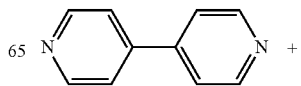

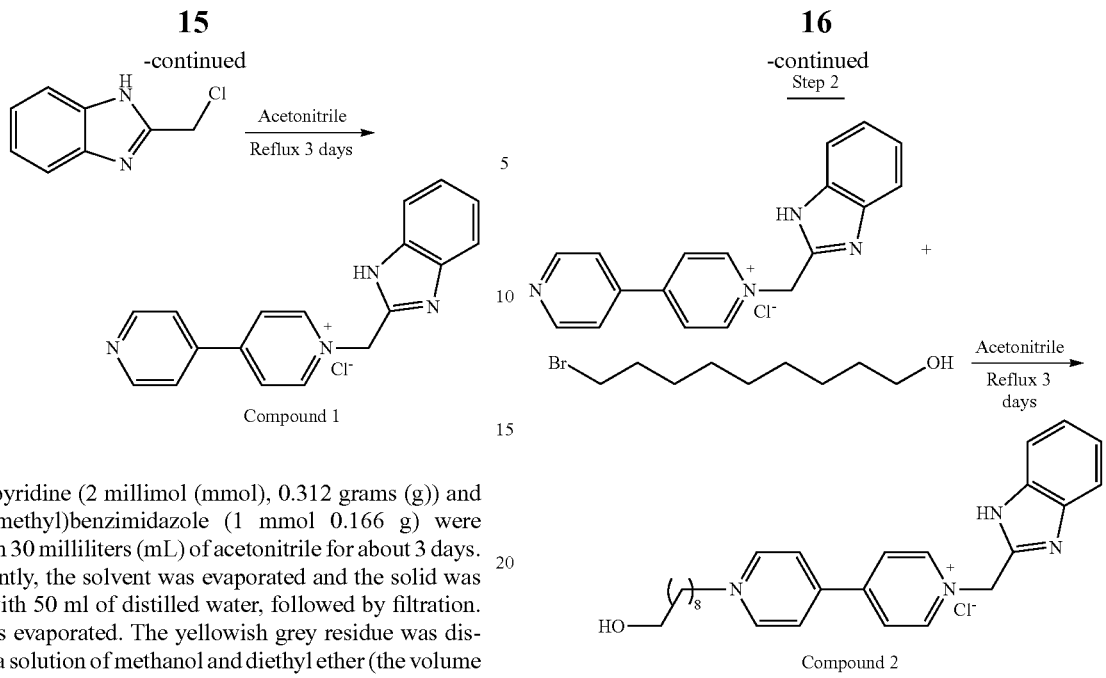

Figure 3:
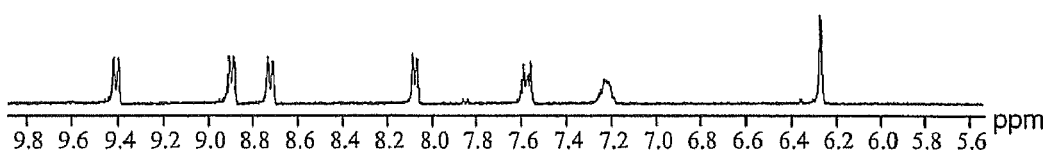
FIG. 3 is a $^1$H NMR spectrum of an exemplary embodiment of an electrochromic material prepared according to Example 1.

4,4-Dipyridine (2 millimol (mmol), 0.312 grams (g)) and 2-(chloromethyl)benzimidazole (1 mmol 0.166 g) were refluxed in 30 milliliters (mL) of acetonitrile for about 3 days. Subsequently, the solvent was evaporated and the solid was washed with 50 ml of distilled water, followed by filtration. Water was evaporated. The yellowish grey residue was dissolved in a solution of methanol and diethyl ether (the volume ratio of methanol to diethyl ether is 1:1) and kept overnight. The solution was filtered and dried to give Compound 1, which is a yellowish grey crystalline material. The deuterium nuclear magnetic resonance CH NMR) spectrum of Compound 1 is shown in FIG. 3.

EXAMPLE 2

Synthesis of Compound 2

The compound of Formula 2 ('Compound 2') was synthesized according to the following reaction scheme (2).

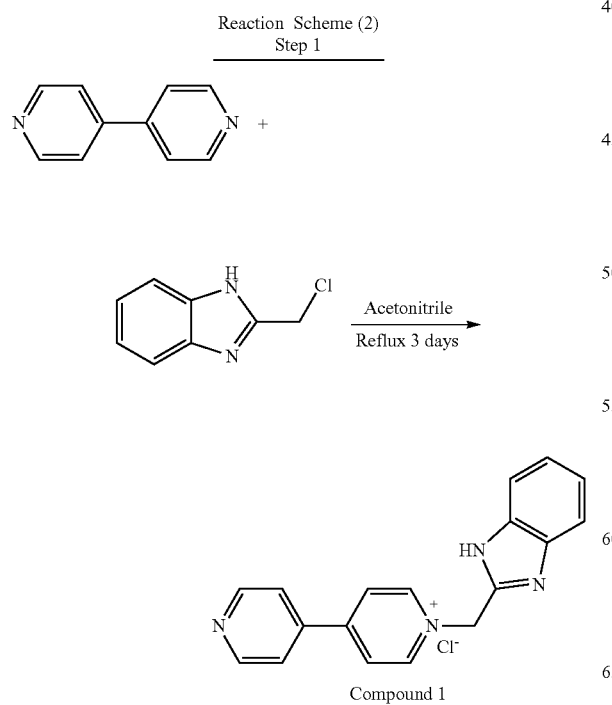

1 mmol (0.322 g) of Compound 1 and 1 mol (0.223 g) of 9-bromo-1-nonanol were refluxed in 30 mL of acetonitrile for 3 days. Subsequently, the solvent was evaporated and the solid was washed with 50 ml of distilled water, followed by filtration. Water was evaporated. The yellowish grey residue was dissolved in a solution of methanol and ether (the volume ratio of methanol to ether is 1:1) and kept overnight. The solution was filtered and dried to give Compound 2. Compound 2 is a yellowish grey crystalline material. The molecular structure of Compound 2 was confirmed by $^1$H NMR spectroscopy.

EXAMPLE 3

Synthesis of Compound 3

The compound of Formula 3 ('Compound 3') was synthesized according to the following reaction scheme (3).

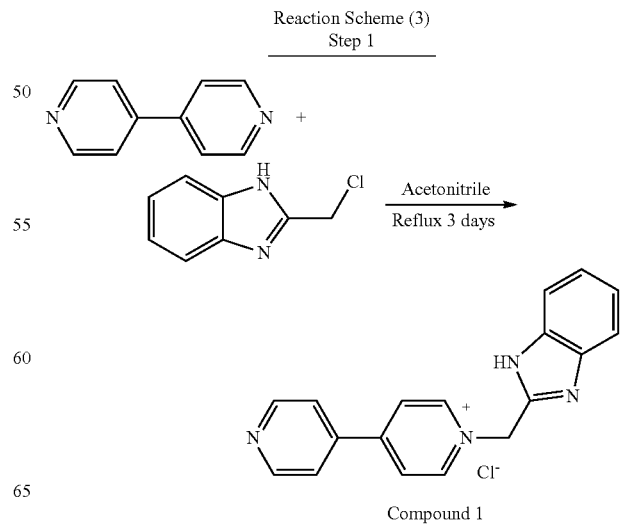

17
-continued
Step 2

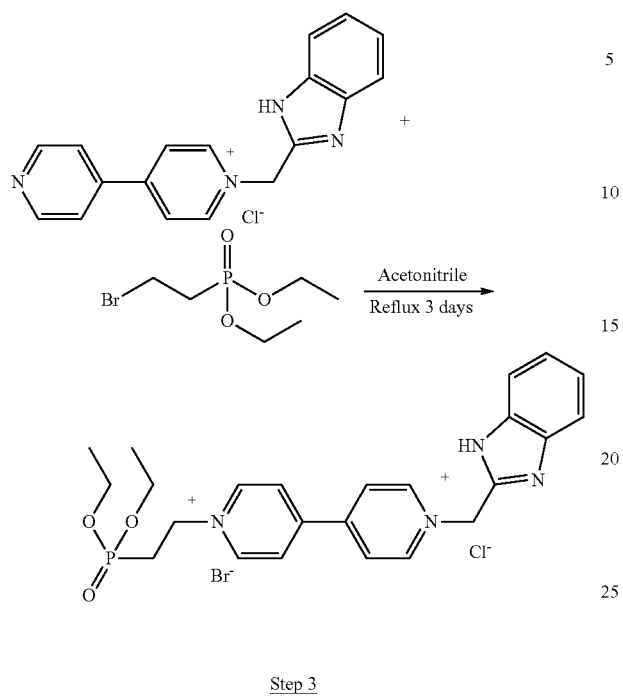

Step 3

Compound 3

18
EXAMPLE 4

Synthesis of Compound 4

The compound of Formula 4 ('Compound 4') was synthesized according to the following reaction scheme (4).

Reaction Scheme (4)
Step 1

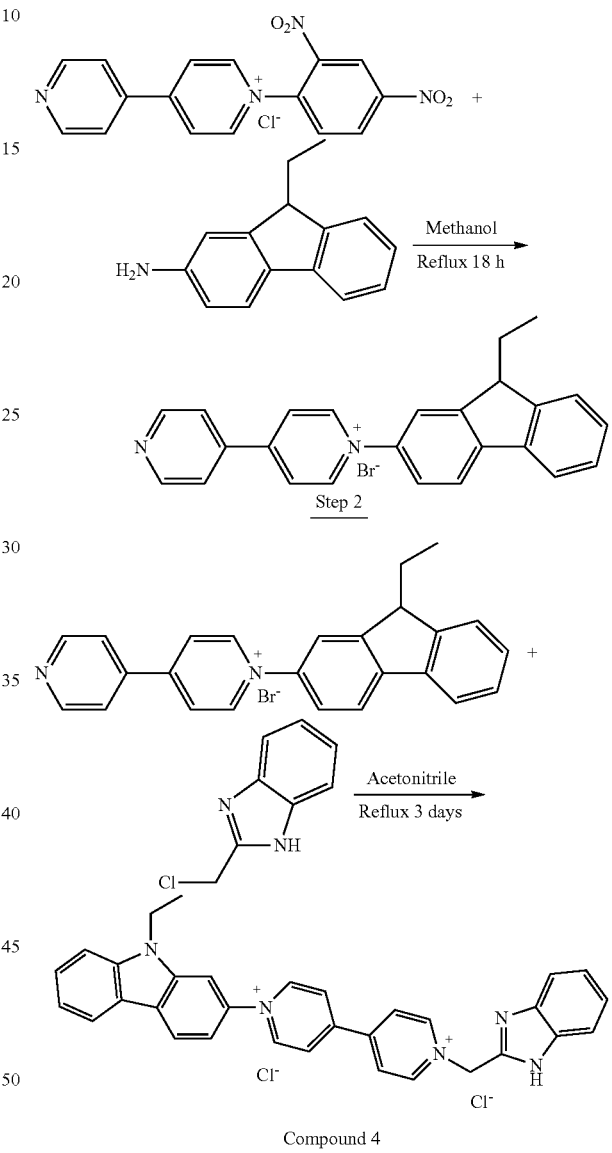

Compound 4

Figure 4:
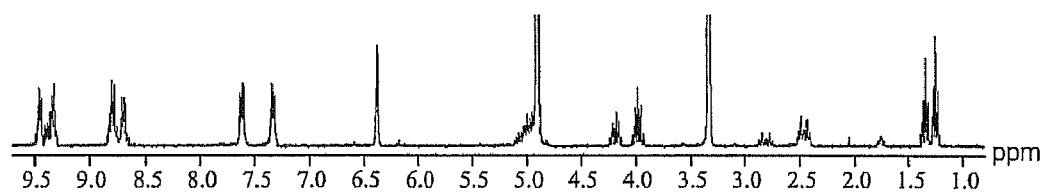
FIG. 4 is a $^1$H NMR spectrum of an exemplary embodiment of an electrochromic material prepared according to Example 3.

1 mmol (0.322 g) of Compound 1 and 1 mol (0.245 g) of diethyl 2-bromoethylphosphonate were refluxed in 30 mL of acetonitrile for about 3 days. Subsequently, the solvent was evaporated and the residual solid was washed with 50 ml of distilled water, followed by filtration. Water was evaporated. The yellowish brown residue was recrystallized from a solution of methanol, chloroform and hexane (the volume ratio of methanol to chloroform to hexane is 1:1:1). The crystals obtained from the yellowish brown residue were allowed to stand in 80 mL of 35% hydrochloric acid at 75° C. for one day. The solution was filtered to obtain a yellowish brown solid. The solid was dissolved in methanol, filtered and reprecipitated from acetone to yield Compound 3. The $^1$H NMR spectrum of Compound 3 is shown in FIG. 4.

1-2,4-Dinitrophenyl-4,4'-bipyridinium chloride (1 mmol, 0.358 g) and 3-amino-(9-ethylcarbazole) (1 mmol 0.21 g) were refluxed in 30 mL of methanol for 18 hours (h). The solvent was evaporated and the solid was washed with 50 ml of distilled water, followed by filtration. The water was subsequently evaporated. The red residue that was formed was dissolved in a solution of methanol and chloroform (the volume ratio of methanol to chloroform was 1:1) and kept overnight. The solution was filtered and dried to give 1-(3-(9-ethylcarbazolyl)-4,4-bipyridinium chloride in the form of a brownish red crystalline material.

1-(3-(9-Ethylcarbazolyl)-4,4-bipyridinium chloride (1 mmol) and 2-(chloromethyl)benzimidazole (1 mmol, 0.166 g) was refluxed in 30 mL of acetonitrile for 3 days. The solvent was evaporated to leave behind a deep red solid. The deep red solid was washed with 50 ml of distilled water, followed by filtration. The water was subsequently evaporated. The deep red residue was recrystallized from a solution of methanol and diethyl ether (the volume ratio of methanol to diethyl ether was 1:1) to yield Compound 4. The molecular structure of Compound 4 was confirmed by $^1$H NMR spectroscopy.

EXAMPLE 5

Synthesis of Compound 5

The compound of Formula 5 ('Compound 5') was synthesized according to the following reaction scheme (5).

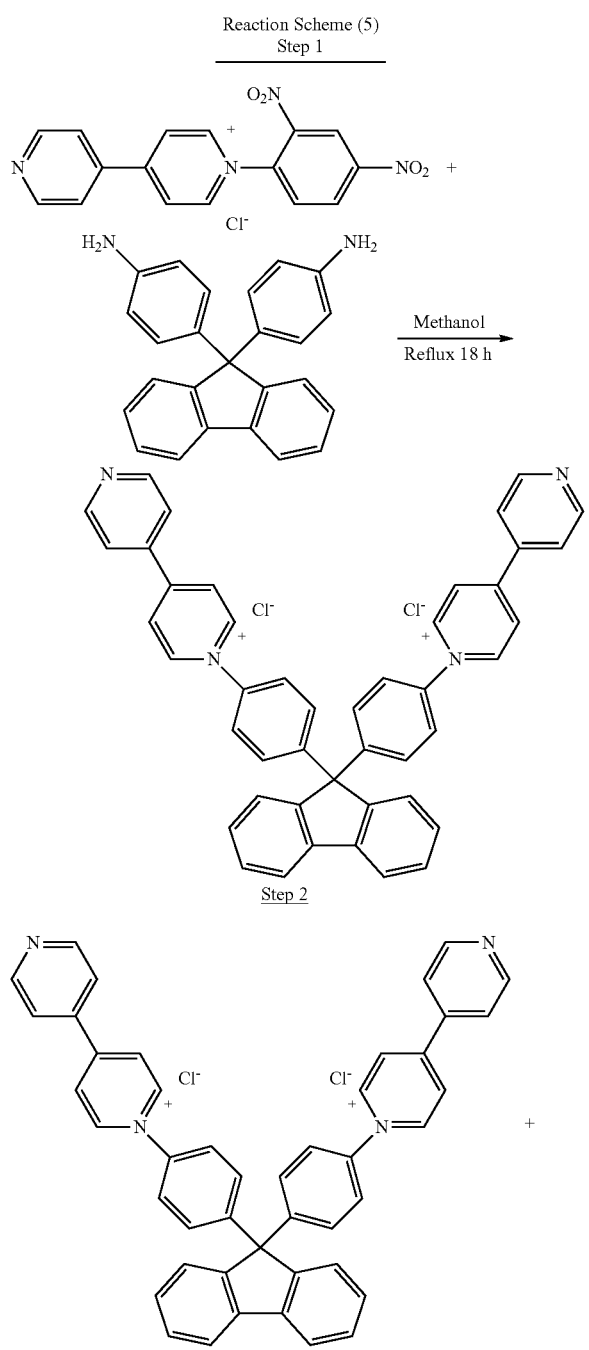

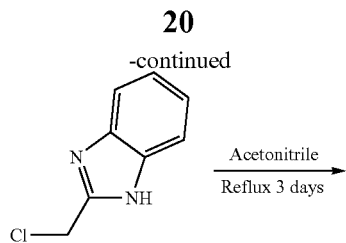

Figure 5:
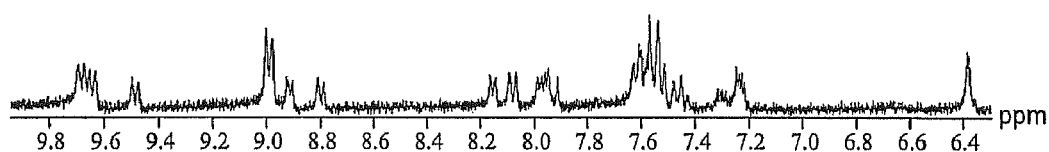
FIG. 5 is a $^1$H NMR spectrum of an exemplary embodiment of an electrochromic material prepared according to Example 5.

Specifically, Compound 5 was prepared by the same method described in Example 4, except that in the place of 1 mmol of 3-amino-(9-ethylcarbazole), 0.5 mmol (0.174 g) of 9,9-bis(4-aminophenyl)fluorine was used. The $^1$H NMR spectrum of Compound 5 is shown in FIG. 5.

EXPERIMENTAL EXAMPLE 1

Fabrication of Electrochromic Devices and Evaluation of Electrochromic Properties of Electrochromic Materials An indium tin oxide (ITO) coated transparent electrode was formed on a glass substrate, and a TiO$_2$ nanoparticle thin film was formed on the ITO. An aqueous solution of each of the electrochromic materials prepared in Examples 1-5 was dropped on the nanoparticle thin film. After the solvent was evaporated, the resulting structure was covered with another ITO-coated glass substrate. Spacers were disposed between two ITO-coated glass substrates to maintain a cell gap, followed by sealing of an internal chamber formed between the two ITO-coated glass substrates. An electrolyte solution was injected into the cell to fabricate the electrochromic test device. For Compounds 1 and 2, the electrolyte solution was a solution of LiClO$_4$ and ferrocene (functioning as electrolytes) dissolved in N-methylpyrrolidone (NMP). For Compounds 3, 4 and 5, the electrolyte solution was a solution of LiClO$_4$ and ferrocene (functioning as electrolytes) dissolved in gamma-butyrolactone (GBL).

Changes in the color of the electrochromic devices were observed when the respective voltages indicated in Table 1 were applied to the devices. The results are shown in Table 1.

TABLE 1

| | Color changes in response to applied voltages (V) | | | | | |
|---|---|---|---|---|---|---|
| Compound No. | Voltage (V) | Color | Voltage (V) | Color | Voltage (V) | Color |
| 1 | −2.0 | Red | 0 | Colorless | +2.0 | Red |
| 2 | −1.2 | Blue | 0 | Colorless | +1.2 | Blue |
| 3 | −2.0 | Colorless | 0 | Colorless | +1.1 | Violet |
| 4 | −2.0 | Green | 0 | Colorless | +2.0 | Green |
| 5 | −1.1 | Green | 0 | Colorless | +1.1 | Green |

As apparent from the results in Table 2, the electrochromic devices, each of which includes an electrochromic layer in the form of a solution or gel produced various colors, e.g., red as well as blue and violet upon the application of a voltage.

In addition, the electrochromic properties of Compounds 2 and 3 did not change after the voltage was removed, thus indicating that these compounds had a good "image memory". In other words, Compounds 2 and 3 upon changing color because of the applied voltage did not return to their original colors upon removal of this voltage.

Although exemplary embodiments have been described herein with reference to the foregoing preferred embodiments, those skilled in the art will appreciate that various modifications and changes are possible without departing from the spirit of the exemplary embodiments as disclosed in the accompanying claims. Therefore, it is to be understood that such modifications and changes are encompassed within the scope of the exemplary embodiments.

What is claimed is:

1. An electrochromic material represented by the Formula 3:

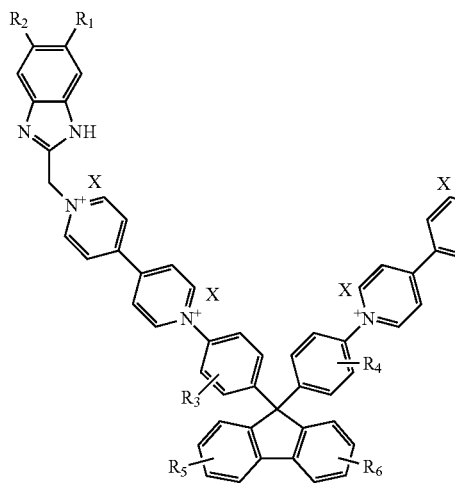

Formula (3)

wherein $R_1$ and $R_2$ are each independently selected from the group consisting of hydrogen, halogen, CN, OH, COOH, $C_1$-$C_{20}$ alkyl, $C_3$-$C_{20}$ cycloalkyl, $C_2$-$C_{20}$ alkenyl, $C_1$-$C_{20}$ alkoxy and $C_5$-$C_{12}$ aryl, wherein each X is selected from the group consisting of halides, $PF_6^-$, $BF_4^-$, $BH_4^-$ and $CF_3SO_3^-$, and wherein $R_3$, $R_4$, $R_5$ and $R_6$ are independently selected from the group consisting of hydrogen, halogen, CN, OH, COOH, $C_1$-$C_{20}$ alkyl, $C_3$-$C_{20}$ cycloalkyl, $C_2$-$C_{20}$ alkenyl, $C_1$-$C_{20}$ alkoxy, $C_5$-$C_{12}$ aryl, $C_5$-$C_{12}$ heteroaryl, carbazolyl, fluorenyl and spirofluorenyl.

2. The electrochromic material of claim 1 wherein at least one of $R_3$, $R_4$, $R_5$ and $R_6$ has an end group selected from the group consisting of $CH_3$, OH, SH, COOH, $PO_3H_2$, halogen, CN and $COH_3$.

3. The electrochromic material of claim 1, wherein the electrochromic material of Formula 3 is one represented by Formula 8:

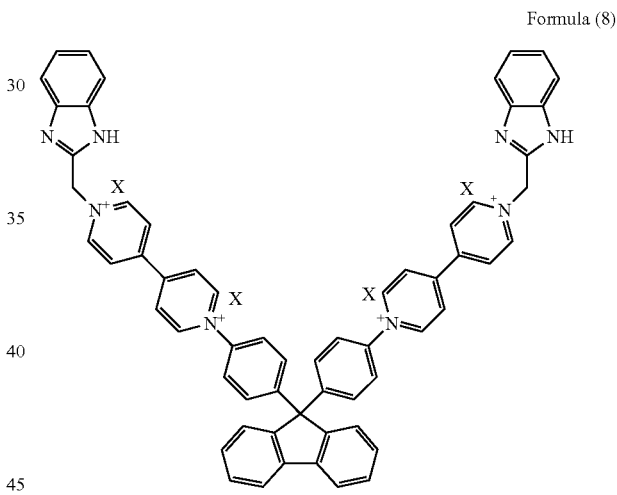

Formula (8)

wherein each X is selected from the group consisting of halides, $PF_6^-$, $BF_4^-$, $BH_4^-$ and $CF_3SO_3^-$.

* * * * *